US012446873B2

(12) United States Patent
Sauer

(10) Patent No.: US 12,446,873 B2
(45) Date of Patent: Oct. 21, 2025

(54) SUTURE SECURITY DEVICE FOR MINIMALLY INVASIVE SURGICAL SUTURING

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 329 days.

(21) Appl. No.: 17/604,582

(22) PCT Filed: Apr. 24, 2020

(86) PCT No.: PCT/US2020/029688

§ 371 (c)(1),
(2) Date: Oct. 18, 2021

(87) PCT Pub. No.: WO2020/219791

PCT Pub. Date: Oct. 29, 2020

(65) Prior Publication Data

US 2022/0192661 A1 Jun. 23, 2022

Related U.S. Application Data

(60) Provisional application No. 62/838,281, filed on Apr. 24, 2019.

(51) Int. Cl.
*A61B 17/06* (2006.01)

(52) U.S. Cl.
CPC .................. *A61B 17/06061* (2013.01); *A61B 2017/06142* (2013.01)

(58) Field of Classification Search
CPC ...... A61B 17/0601; A61B 2017/06142; A61B 17/0483; A61B 17/0491; A61B 17/06114
See application file for complete search history.

(56) References Cited

U.S. PATENT DOCUMENTS

| | | | |
|---|---|---|---|
| 6,004,332 | A | 12/1999 | Yoon et al. |
| 9,079,006 | B1 | 7/2015 | Ovcharchyn et al. |
| 2006/0069397 | A1 | 3/2006 | Nobles et al. |

(Continued)

FOREIGN PATENT DOCUMENTS

| | | |
|---|---|---|
| CN | 101027001 | 5/2010 |
| EP | 0 609 020 | 8/1994 |

(Continued)

OTHER PUBLICATIONS

International Search Report and Written Opinion for PCT/US20/29688, filed Apr. 24, 2020, mailed Jul. 29, 2020.

(Continued)

*Primary Examiner* — Kathleen S Holwerda
*Assistant Examiner* — Serenity A Miller
(74) *Attorney, Agent, or Firm* — Michael E. Coyne

(57) ABSTRACT

A suture security device is disclosed. The suture security device also includes a latch, a plate, and an actuator coupled to the latch and operable to move the latch away from the plate. The suture security device may also include a first latch array, a second latch array, a plurality of plates, a first actuator coupled to the first latch array and operable to move the first latch array away from the plurality of plates, and a second actuator coupled to the second latch array and operable to move the second latch array away from the plurality of plates.

11 Claims, 11 Drawing Sheets

(56) References Cited

U.S. PATENT DOCUMENTS

| | | | | |
|---|---|---|---|---|
| 2008/0269786 | A1* | 10/2008 | Nobles | A61B 17/0469 606/144 |
| 2015/0190132 | A1 | 7/2015 | Hamilton et al. | |
| 2016/0151064 | A1 | 6/2016 | Nobles et al. | |
| 2020/0297345 | A1* | 9/2020 | Pizanias | A61B 17/085 |

FOREIGN PATENT DOCUMENTS

| | | |
|---|---|---|
| WO | 1996025102 | 8/1996 |
| WO | 2000019913 | 4/2000 |
| WO | 2006037039 | 4/2006 |
| WO | 2007138284 | 12/2007 |
| WO | 2012148379 | 11/2012 |
| WO | 2020251986 | 12/2020 |

OTHER PUBLICATIONS

Supplementary European Search Report for EP 20795303.5 filed Oct. 19, 2021, dated Oct. 25, 2022.

China Office Action for corresponding application No. 2020800305893, mailed Mar. 18, 2024, 20 pages.

First Examination Report for Indian Application No. 202117047857, filed Oct. 21, 2021, dated Jun. 14, 20241. 3 pages.

* cited by examiner

SUTURE SECURITY DEVICE FOR MINIMALLY INVASIVE SURGICAL SUTURING

RELATED APPLICATIONS

This application is a national stage application, filed under 35 U.S.C. § 371, of International Patent Application No. PCT/US20/29688, filed Apr. 24, 2020 and entitled "SUTURE SECURITY DEVICE FOR MINIMALLY INVASIVE SURGICAL SUTURING," which claims priority to U.S. Provisional Patent Application No. 62/838,281 filed Apr. 24, 2019 and entitled "SUTURE SECURITY DEVICE FOR MINIMALLY INVASIVE SURGICAL SUTURING," the contents of each of which is hereby incorporated by reference in its entirety.

FIELD

The claimed invention relates generally to surgical instruments for automated suturing, and more particularly to such a surgical instrument having a suture security device to ensure sutures are not deployed prematurely.

BACKGROUND

Surgical instruments for automated suturing, such as the RD180® device from LSI Solutions, Inc., Victor, NY (www.lsisolutions.com) provide a reliable and effective way to deliver a suture stitch remotely through a minimally invasive surgical opening. Such devices typically have a suture loaded therein, whereby the suture has a metal tube or ferrule attached to the end of the suture. The ferrule sits in a ferrule holder on one side of a tissue gap on the distal end of the suturing device. In axial alignment with the held ferrule is a needle on the opposite side of the device's tissue gap. The device is oriented to place a targeted tissue location within the tissue gap, and a needle actuator is engaged to move the needle through the tissue in the gap, into interference contact with the ferrule, causing the ferrule to couple with the needle. The needle actuator is released, thereby causing the needle to retract back through the tissue in the tissue gap, also pulling the suture attached to the ferrule back through the tissue and this creating a stitch in the tissue.

In general, ferrule holders are very effective for holding the ferrules in alignment with the needle of the device until a stitch is made. However, automated suturing devices continue to be developed for ever-expanding applications, the environment within which the device may be used and/or the flexibility and steerability of the device shaft which is needed to position the tissue gap onto target tissue may cause the ferrule held in the ferrule holder to come loose prior to when the needle is actuated. If this happens, the suturing device may not work as intended.

Therefore, there is a need for a suture security device for such automated suturing devices so have a high assurance for certain suturing applications that the ferrule remains in its ferrule holder until the needle is ready to pick it up.

SUMMARY

A suture security device is disclosed. The suture security device also includes a latch, a plate, and an actuator coupled to the latch and operable to move the latch away from the plate.

Another suture security device is also disclosed. The suture security device includes a first latch array, a second latch array, a plurality of plates, a first actuator coupled to the first latch array and operable to move the first latch array away from the plurality of plates, and a second actuator coupled to the second latch array and operable to move the second latch array away from the plurality of plates.

An additional suture security device is also disclosed. The suture security device also includes a housing, a first latch array having a plurality of latches coupled to the housing, a second latch array having a plurality of latches coupled to the housing and interlaced with the first latch array, a plurality of plates, a first actuator coupled to the first latch array and operable to move the first latch array away from the plurality of plates, and a second actuator coupled to the second latch array and operable to move the second latch array away from the plurality of plates.

BRIEF DESCRIPTION OF THE DRAWINGS

FIGS. 2A-2J are exploded views illustrating assembly of another embodiment of a suture security device.

DETAILED DESCRIPTION

Figures 1A, 1B, 1C:
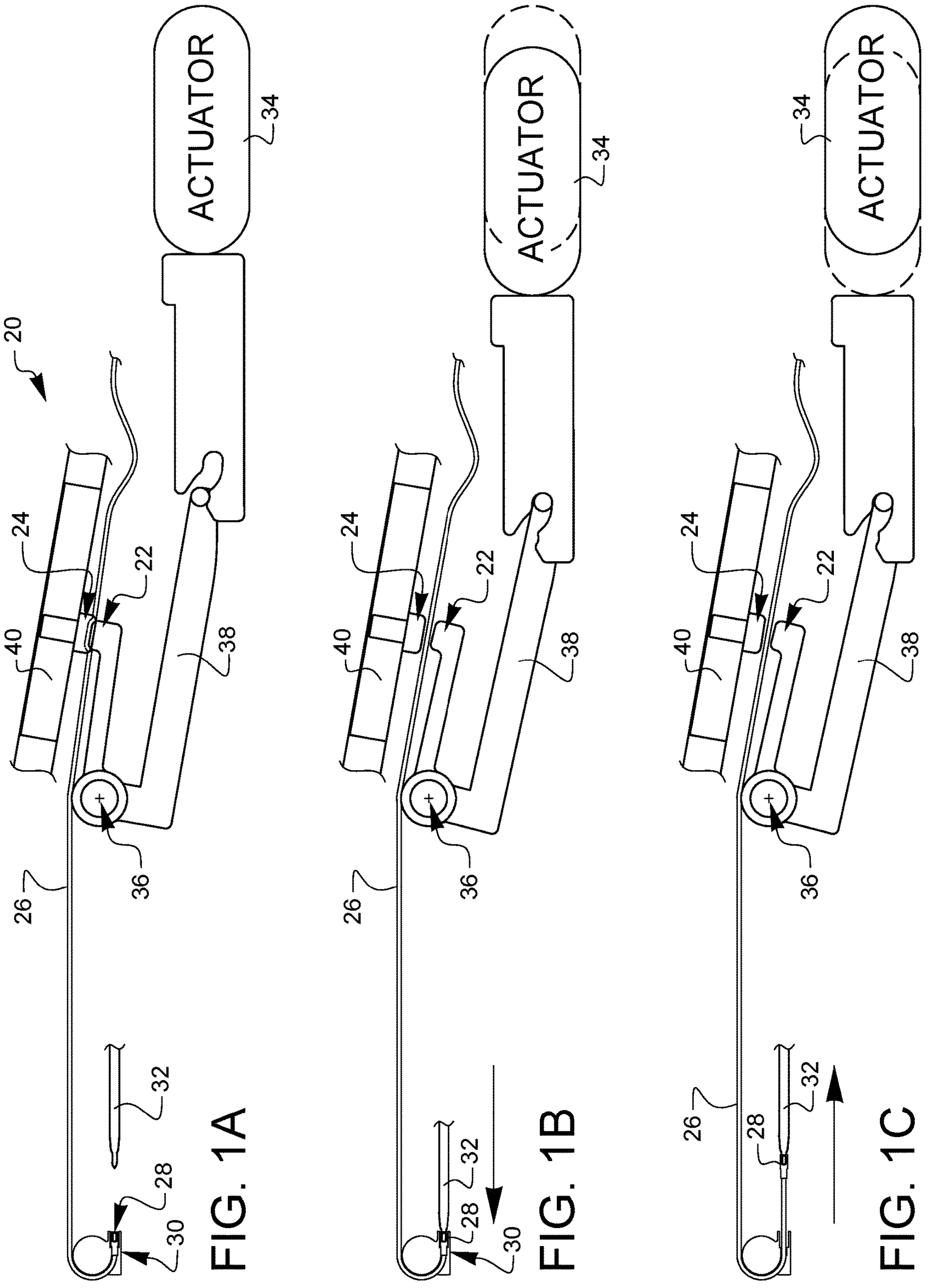
FIGS. 1A-1C are schematic illustrations of one embodiment of a suture security device 20 for surgical suturing.

FIG. 1A is a schematic illustration of one embodiment of a suture security device 20 for surgical suturing. The device has a latch 22 which may be selectively held towards a plate 24. A suture 26 may be placed between the latch 22 and its plate 24. At least one end of the suture 26 has a ferrule 28 coupled to it. The ferrule 28 is placed into a ferrule holder 30 and the suture 26 is routed back towards the latch 22 and plate 24. The suture 26 may be lightly tensioned or otherwise adjusted for length so that the ferrule 28 is held in the ferrule holder 30. The latch 22 may be engaged or held towards the plate 24, gripping the suture 26 therebetween in order to maintain the suture position and provide additional insurance that the ferrule 28 will not prematurely leave the ferrule holder 30. As described above in the background, a needle 32 is axially aligned opposite from the loaded ferrule 28.

As schematically illustrated in FIG. 1B, the needle 32 may be actuated towards and into contact with the ferrule 28. At approximately the same time, or any desired relative time, an actuator 34 may also be engaged to move the latch 22 away from the plate 24 in order to release the held suture 26. At the point of FIG. 1B, the needle 32 has properly engaged the ferrule 28, so there is no need to secure the ferrule 28 in the ferrule holder 30 at this time. By releasing the latch 22's grip on the suture 26, the needle 32 is then free to retract as shown in FIG. 1C, pulling the ferrule 28 and its attached suture 26 back across a tissue gap.

In the embodiment of FIGS. 1A-1B, the actuator 34 which moves the latch 22 away from the plate 24 may be coupled to the actuator for the needle 32, or it may be separately actuated. In the embodiment shown, the latch 22 is pivotable about an axis 36 as moved by a cam linkage 38 coupled to the actuator 34. In this way, the suture 26 is secured until it needs to be released. For some embodiments, the plate 24 may be part of, supported by, or adjacent to a window 40 through which a user can view the held suture 26 and see when it has moved after ferrule pickup in order to remotely verify a successful needle pickup since the distal tip with the needle 32 and ferrule 28 may not be visible to the user.

FIGS. 2A-2J are exploded views illustrating assembly of another embodiment of a suture security device. This device has a plurality of latches, represented by a first latch array 42 and a second latch array 44. The first latch array 42 has a plurality of latches 46, while the second latch array has a plurality of latches 48. In this embodiment, each latch array 42, 44 has six latches 46, 48, respectively, meaning the final unit will be able to secure twelve sutures, six with the first latch array 42 and six with the second latch array 44. Each latch array 42, 44 has its own respective cam linkage 50, 52. Similarly, each latch array 42, 44 has its own respective pivot axis 54, 56. In this embodiment, the second latch array 44 has clearance slots 58 which allow the two latch arrays to be interlaced for a more compact assembly. The compact, interlaced latch array assembly 60 is visible in FIG. 2B.

The latch assembly 60 is placed within an inner housing 62, while the ends of the pivot axes 54, 56 pass out holes 64, 66 on either side (only one side is visible in this view) and are held in place (while still remaining pivotable) by bushings 68, 70.

Figure 2A:
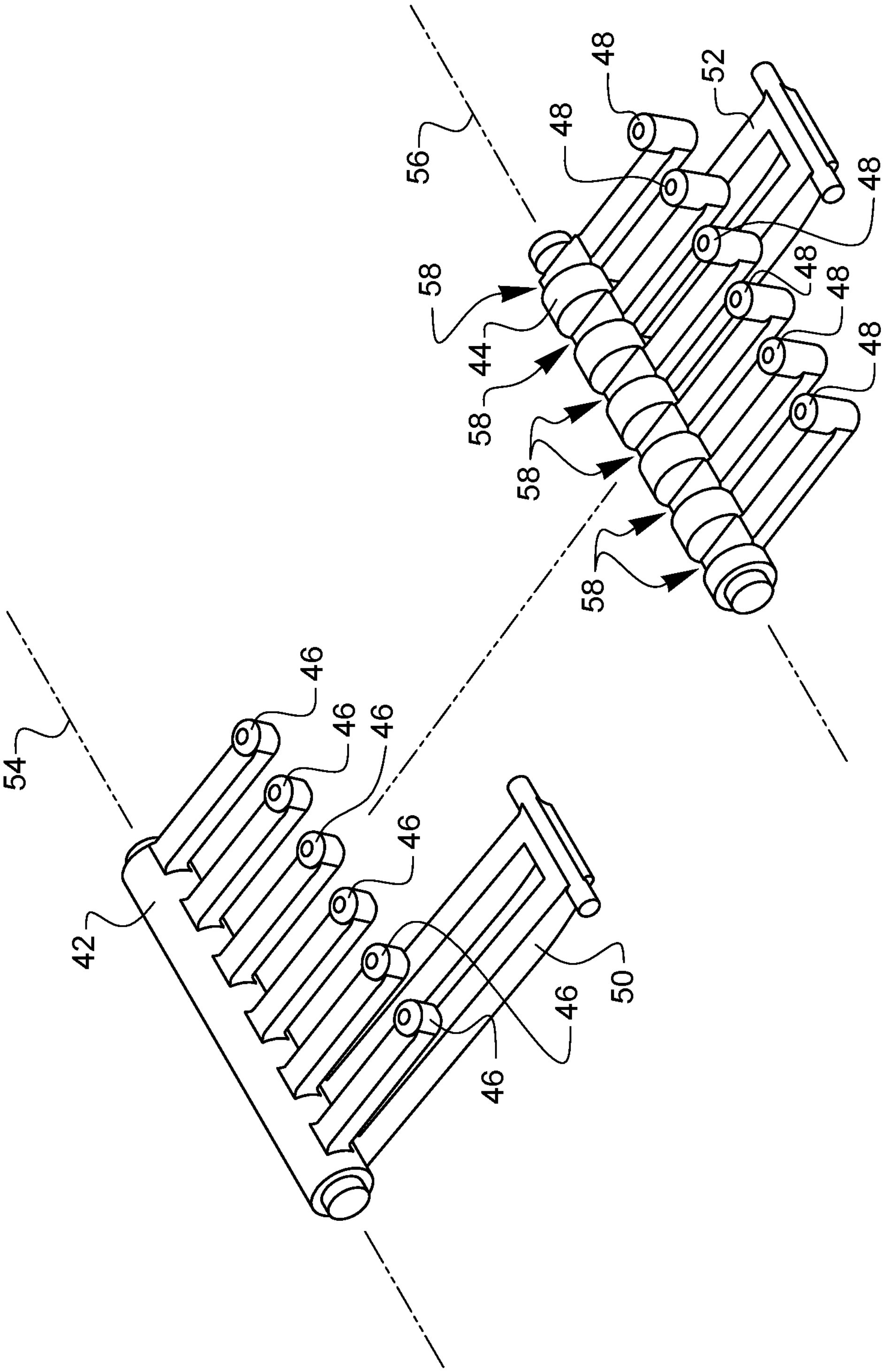
Figure 2B:
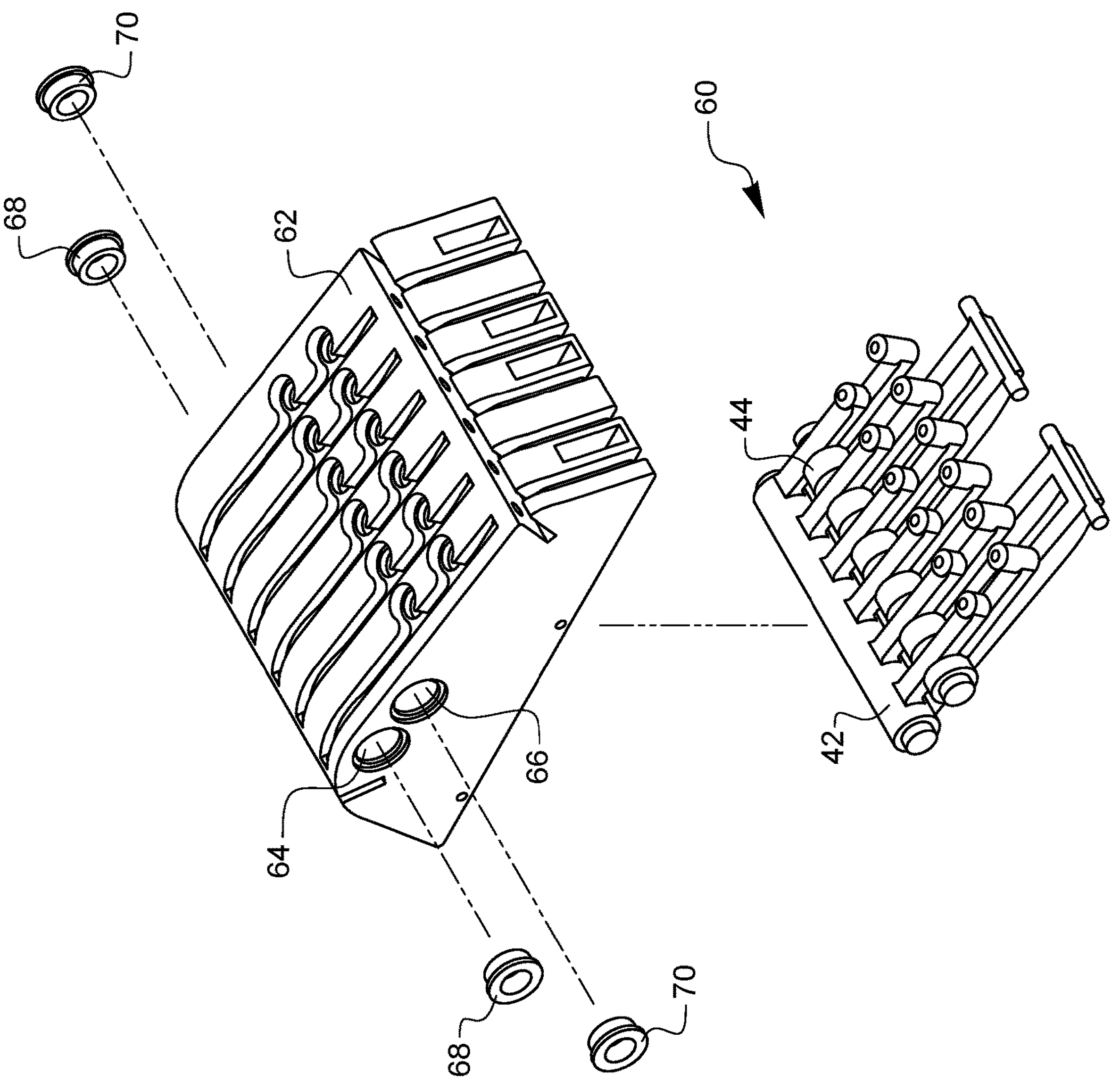
Figure 2C:
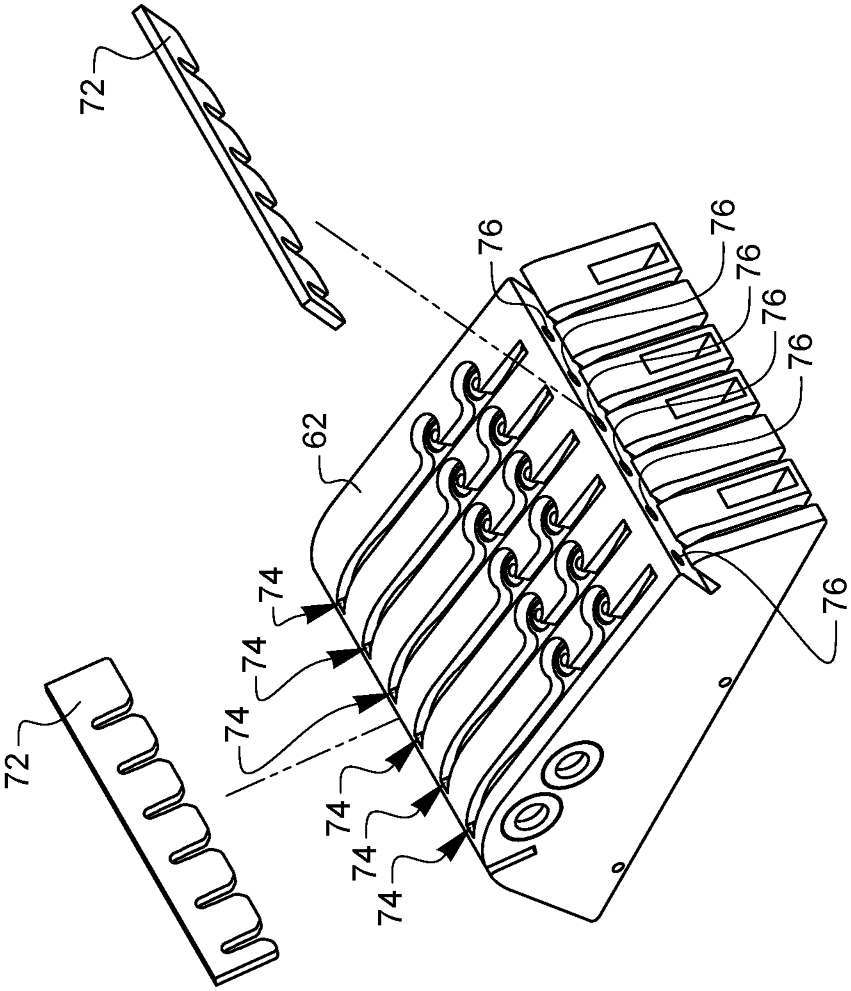

As illustrated in FIG. 2C, optional combs 72 may be provided to interface with the housing and assist with holding tubes (not shown) for guiding suture into the housing 62. Suture will enter through the inner housing 62 in channels 74 from the distal end and exit the inner housing 62 on the proximal end at openings 76.

Figure 2D:
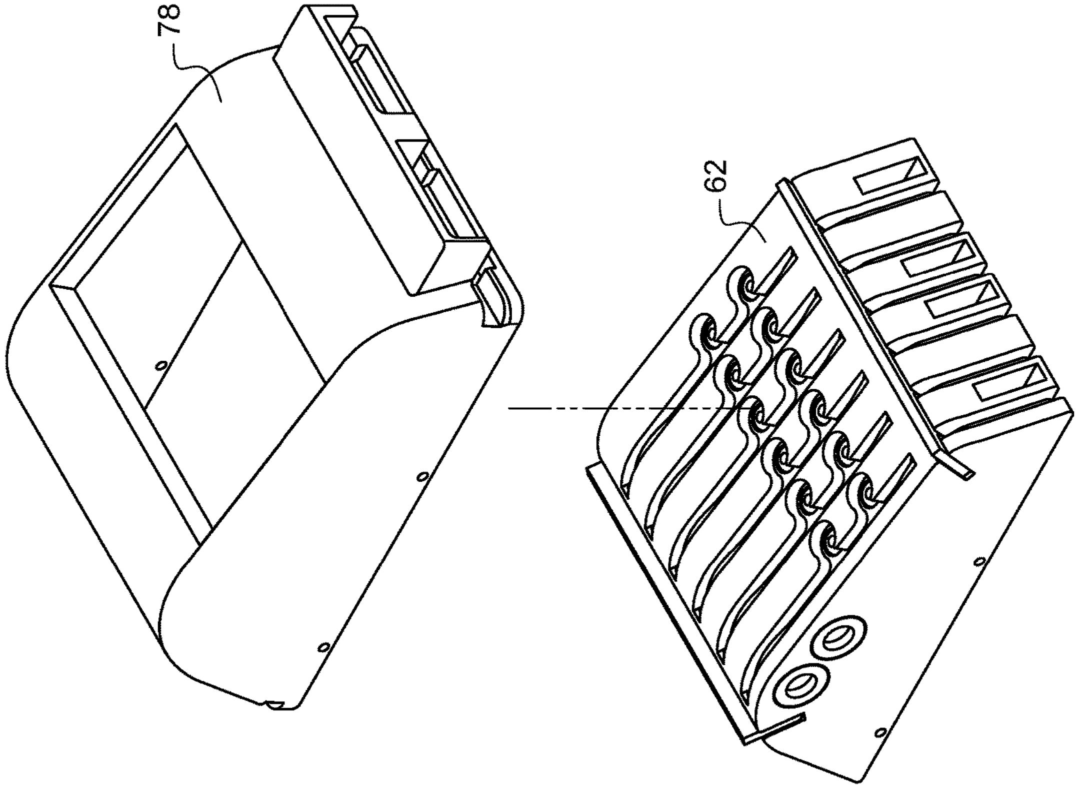
Figure 2E:
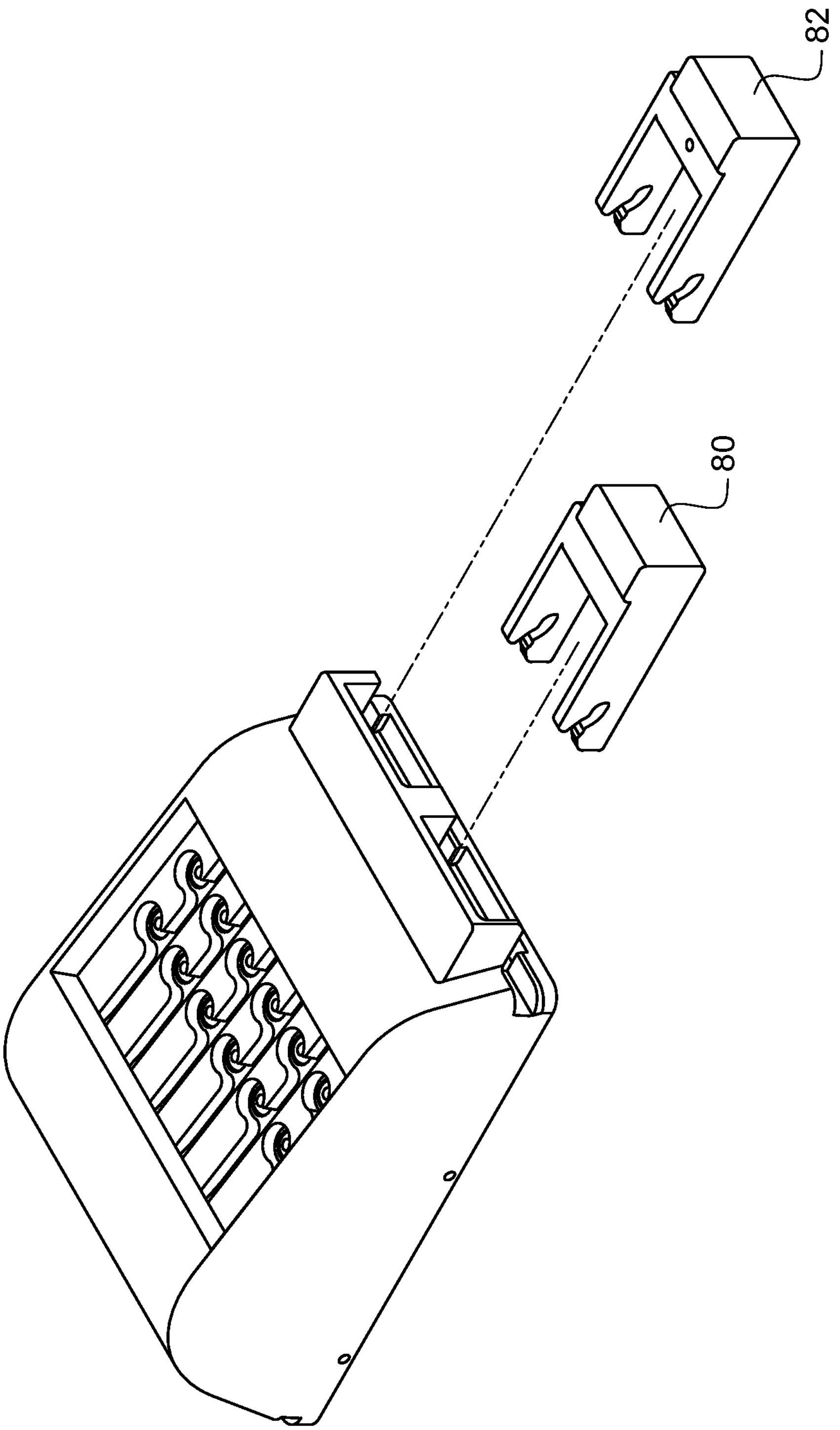

As illustrated in FIG. 2D, an outer housing 78 may be placed over the inner housing 62. As illustrated in FIG. 2E, a first actuator 80 is passed through the outer and inner housings 78, 62 to couple with the cam linkage 50 of the first latch array 42. Similarly, a second actuator 82 is passed through the outer and inner housings 78, 62 to couple with the cam linkage 52 of the second latch array 44.

Figure 2F:
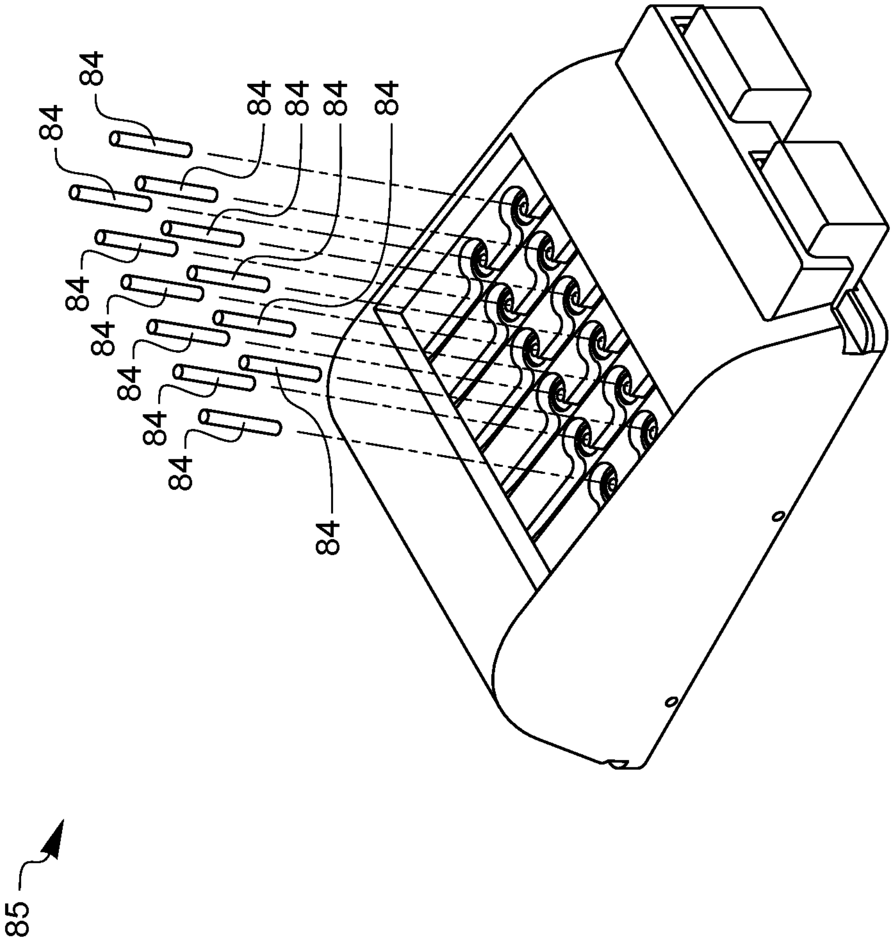

As illustrated in FIG. 2F, temporary assembly posts 84 are placed in alignment holes in each of the latches 46, 48. Individual sutures are routed around each assembly post 84 so that each suture does not run in a straight line.

Figure 2G:
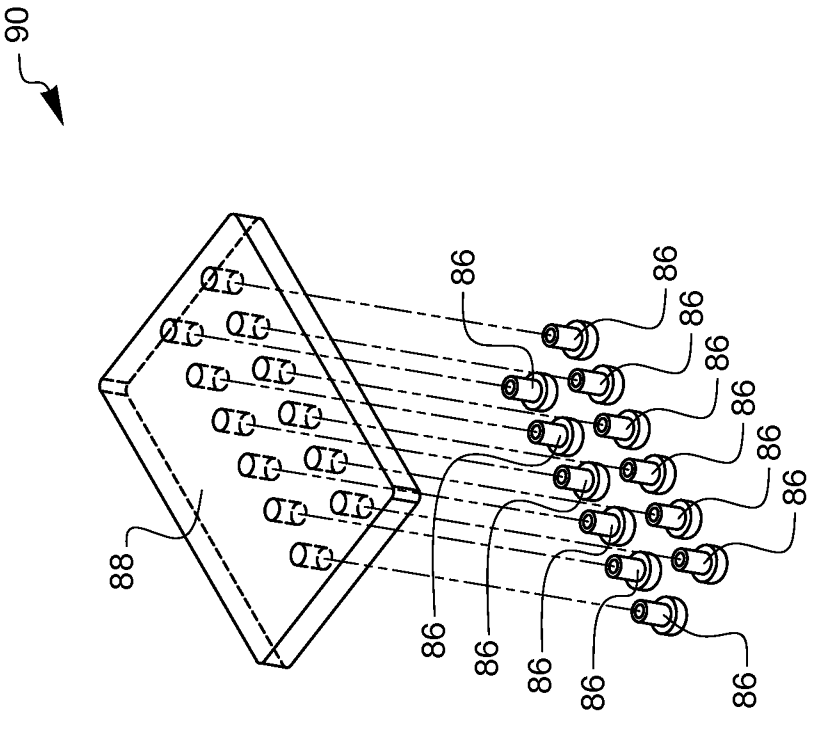

As shown in FIG. 2G, a set of plates 86 are coupled to a transparent window 88 in a pattern which will align with the latches 46, 48 of the previous assemblies. In other embodiments, the plates 86 may be integral with the window, and in still other embodiments, the transparent window may only be translucent or not translucent or transparent at all (in which case the viewing functionality would be lost for such embodiments).

Figure 2H:
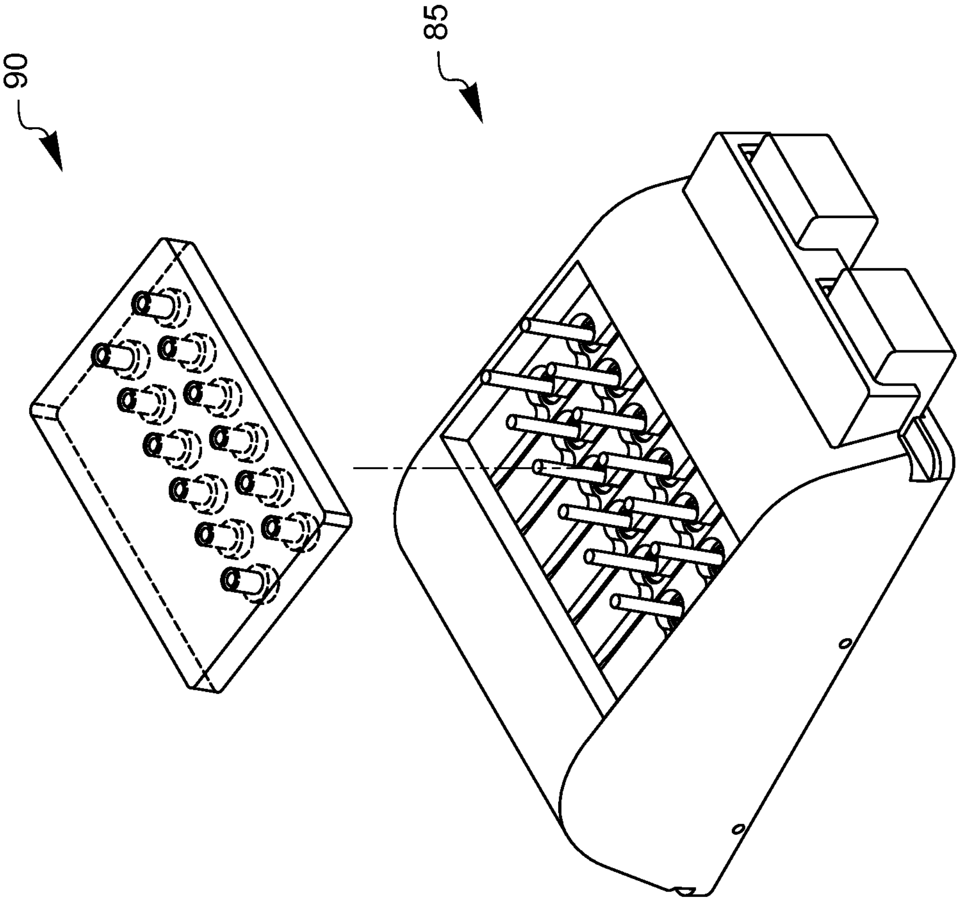

As shown in FIG. 2H, the window and plate assembly 90 from FIG. 2G is placed over the housing assembly 85 from FIG. 2F. Each of the plates 86 has a hole therein which allows the temporary assembly posts to pass through, enabling the plates 86 and the latches 46, 48 to pinch a single suture section therebetween (six held by the first latch array, another six held by the second latch array).

There is not FIG. 2I, as this number looks too similar to the number twenty-one. Then, as shown in FIG. 2J, the temporary assembly posts 84 are removed from the device.

Figure 2J:
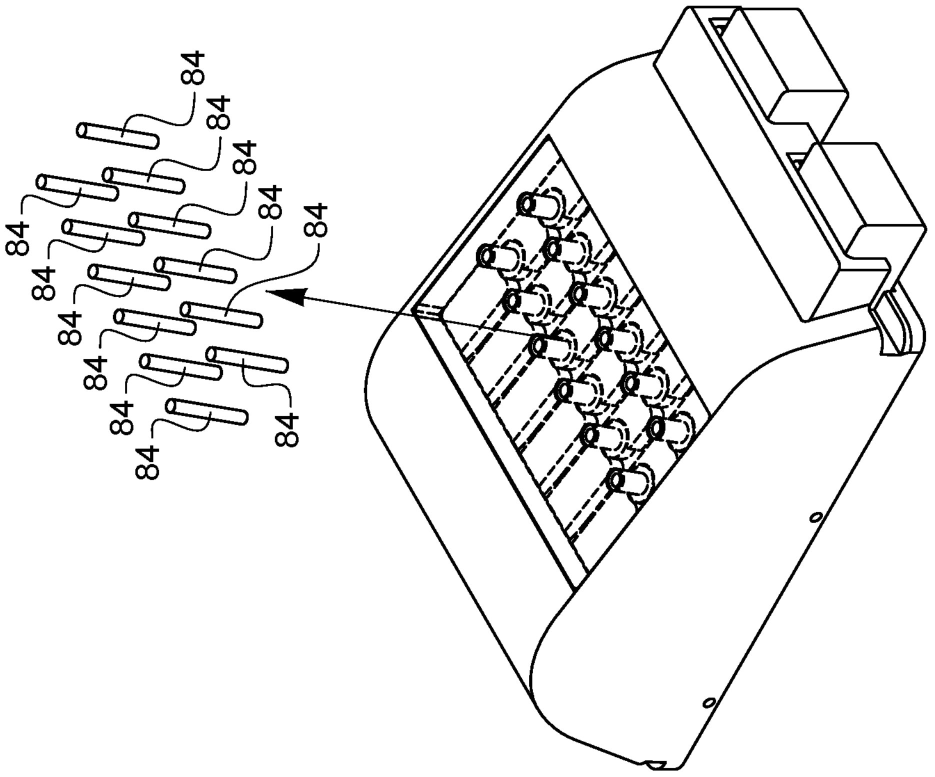
Figure 3:
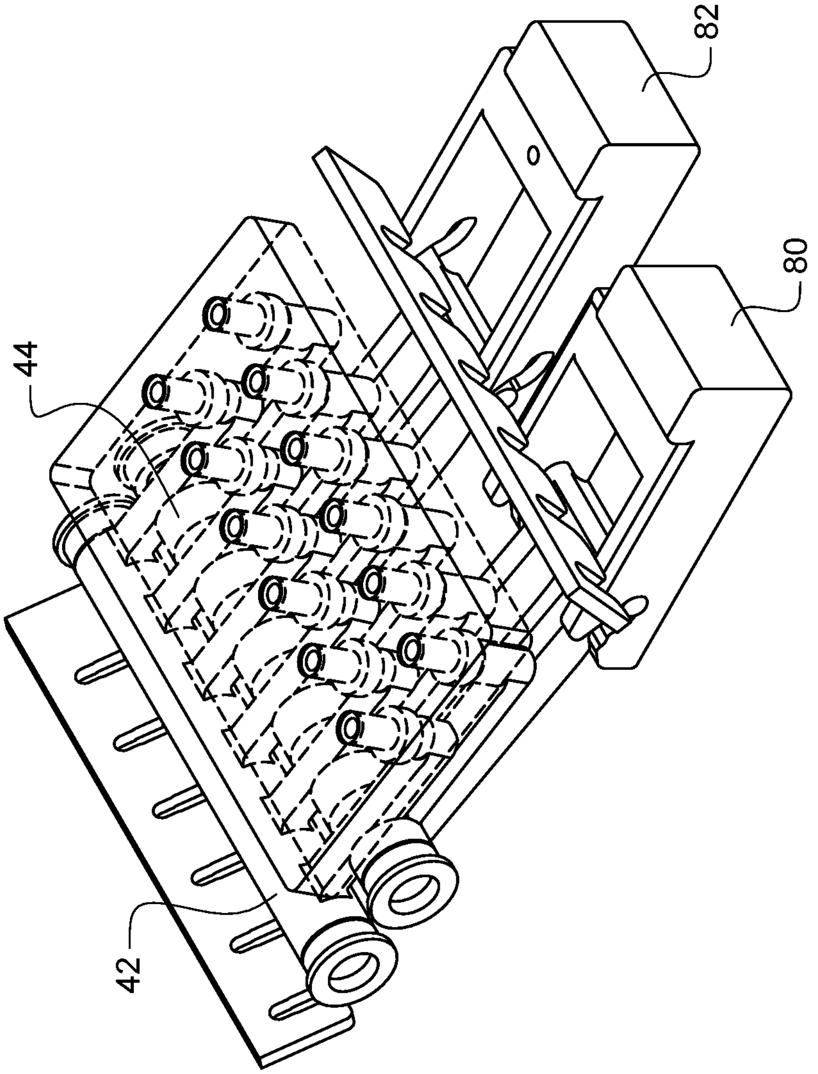
FIG. 3 is a partially exposed view of the assembly of the suture security device It will be appreciated that for purposes of clarity and where deemed appropriate, reference numerals have been repeated in the figures to indicate corresponding features, and that the various elements in the drawings have not necessarily been drawn to scale in order to better show the features.

FIG. 3 is a partially exposed view of the assembly of FIG. 2J where the two latch arrays 42, 44 may be seen pressing their latches up against the corresponding plates. The first actuator 80 will release the sutures held by the first latch array 42, while the second actuator will release the sutures held by the second latch array 44.

Various advantages of a suture security device for minimally invasive suturing have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suture security device for automated surgical suturing, comprising: a first latch array, each of the first latch array being pivotable about a first axis; a first cam linkage, each of the first latch array being coupled to the first cam linkage; a second latch array, each of the second latch array being pivotable about a second axis; a second cam linkage, each of the second latch array being coupled to the second cam linkage; a first plurality of plates, wherein each of the first latch array is configured to be selectively held towards a corresponding one of the first plurality of plates, thereby being configured to grip a suture between each of the first latch array and the corresponding one of the first plurality of plates; a second plurality of plates, wherein each of the second latch array is configured to be selectively held towards a corresponding one of the second plurality of plates, thereby being configured to grip a suture between each of the second latch array and the corresponding one of the second plurality of plates; a first actuator coupled to each of the first latch array by the first cam linkage and operable to move the first latch array away from the first plurality of plates; a second actuator coupled to each of the second latch array by the second cam linkage and operable to move the second latch array away from the second plurality of plates; and one or more combs.

2. The suture security device of claim 1, further comprising a housing and a window coupled to the housing.

3. The suture security device of claim 2, wherein the window is comprised of a transparent material.

4. The suture security device of claim 1, further comprising one or more suture channels.

5. The suture security device of claim 1, further comprising a housing having one or more interior surfaces defining an interior portion.

6. The suture security device of claim 5, wherein each of the one or more combs are removably coupled to a corresponding portion of the housing, each of the one or more combs being configured to secure tubes that are configured to guide suture into an interior portion of the housing.

7. The suture security device of claim 5, wherein a first portion of the first latch array is pivotably coupled to a first portion of the housing, a second portion of the first latch array is pivotably coupled to a second portion of the housing a first portion of the second latch array is pivotably coupled to a third portion of the housing, and a second portion of the second latch array is pivotably coupled to a fourth portion of the housing.

8. The suture security device of claim 5, wherein the first cam linkage and the second cam linkage are disposed within the interior portion of the housing.

9. The suture security device of claim 5, wherein each of the first latch array and the second latch array is disposed within the interior portion of the housing.

10. The suture security device of claim 5, further comprising a housing assembly comprising an inner housing and an outer housing, and wherein the housing is the inner housing of the housing assembly.

11. The suture security device of claim 5, further comprising a housing assembly comprising an inner housing and an outer housing, and wherein the housing is the outer housing of the housing assembly.

* * * * *